United States Patent
Wei

(10) Patent No.: US 8,809,003 B2
(45) Date of Patent: *Aug. 19, 2014

(54) REDUCTION IN FALSE RESULTS IN ASSAY MEASUREMENTS

(71) Applicant: Siemens Healthcare Diagnostics Inc., Tarrytown, NY (US)

(72) Inventor: Tie Q. Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/667,368

(22) Filed: Nov. 2, 2012

(65) Prior Publication Data

US 2014/0127715 A1  May 8, 2014

Related U.S. Application Data

(62) Division of application No. 12/823,953, filed on Jun. 25, 2010, now Pat. No. 8,329,424.

(51) Int. Cl.
*G01N 33/00* (2006.01)

(52) U.S. Cl.
CPC ............. *G01N 33/00* (2013.01); *Y10S 435/962* (2013.01)
USPC ........... 435/7.92; 435/7.9; 435/962; 436/174; 436/518

(58) Field of Classification Search
None
See application file for complete search history.

(56) References Cited

U.S. PATENT DOCUMENTS

| | | | |
|---|---|---|---|
| 4,190,496 A | 2/1980 | Rubenstein | |
| 4,447,526 A | 5/1984 | Rupchock et al. | |
| 4,737,456 A | 4/1988 | Weng et al. | |
| 4,810,635 A | 3/1989 | Ledden et al. | |
| 4,863,876 A * | 9/1989 | Hevey ........................ | 436/537 |
| 5,156,972 A | 10/1992 | Issachar | |
| 5,635,406 A | 6/1997 | Grenier et al. | |
| 6,187,547 B1 | 2/2001 | Legay et al. | |
| 6,410,340 B1 | 6/2002 | Soldin | |
| 7,078,495 B1 | 7/2006 | Kasper et al. | |
| 7,186,518 B2 | 3/2007 | Wang et al. | |
| 7,642,338 B2 | 1/2010 | Wei et al. | |
| 8,329,424 B2 * | 12/2012 | Wei ............................. | 435/7.92 |
| 8,361,717 B2 | 1/2013 | Kim | |
| 2005/0208586 A1 | 9/2005 | Shen | |
| 2007/0122850 A1 | 5/2007 | Teng et al. | |
| 2008/0195062 A1 | 8/2008 | Caprioli | |
| 2009/0042223 A1 | 2/2009 | Wei et al. | |
| 2010/0062459 A1 | 3/2010 | Wei et al. | |
| 2010/0240073 A1 | 9/2010 | Wei et al. | |

OTHER PUBLICATIONS

Kroll et al. "A model for Assessing Interference" Clin Chem 1987 vol. 33m, No. 7 pp. 1121-1123 esp p. 1121 section entitled "The Model" p. 1121 section entitled "Experimental Design" and Table.
Jay et al. "Characterization and Mathematical Correction of Hemolysis Interference in Selected Hitachi 717 Assays" Clin Chem 1993 v39, No. 9 pp. 1804-1810 entire document.
Glick et al. "Practical Usesof Serum Indices to Reduce Errors from Lipemia, Icterus, and Hemolysis" Clin Chem 1990 v 36 n(6) p. 1008, Abstract No. 0262 Abstract only.
Kroll et al. "Rationale for Using Multiple Regression Analysis with Complex Interferences" Euro J. Clin Chem Clin Biochem 1992 vol. 30 pp. 415-424 entire document.
Glick et al. "Graphical Comparisons of Interferences in Clinical Chemistry Instrumentation" Clin Chem 1986 v32 n3 pp. 470-475 entire document.
Lippolis, et la. "Optimization of a Fluorescence Polarization Immunoassay for Rapid Quantification of Deoxynivalenol in Durum Wheat-Based Products" Journal of Food Protection vol. 69, No. 11, 2006 pp. 2712-2719 entire document.
Weijland et al., "Elongation Factor Tu D138N, a Mutant with Modified Substrate Specificity, as a Tool to Study Energy Consumption in Protein Biosynthesis", Biochemistry 1994, 33, pp. 10711-10717.
Weijland et al., "The Purification and Characterization of the Catalytic Domain of Src Expressed in *Schizosaccharomyces pombe*", Eur. J. Biochem. 240, pp. 756-764 (1996).
European Supplementary Search Report and Written Opinion of European Patent Application No. EP 11798829 dated Nov. 21, 2013.

* cited by examiner

*Primary Examiner* — Gary W Counts
(74) *Attorney, Agent, or Firm* — Theodore J. Leitereg

(57) ABSTRACT

Methods and reagents are disclosed for detecting a false result in an assay measurement for determining a concentration of an analyte in a sample suspected of containing the analyte. The method comprises measuring assay signal resulting from background only and measuring assay signal resulting from the presence of analyte in the sample plus background and subtracting the first measurement from the second measurement to determine the concentration of analyte in the sample. For example, a measurement result 1 is determined by means of an assay conducted on a portion of the sample where analyte in the sample is substantially sequestered and a measurement result 2 is determined by means of the assay conducted on an equal portion of the same sample where analyte in the sample is substantially non-sequestered. Measurement result 1 is subtracted from measurement result 2 to determine the concentration of analyte in the sample.

10 Claims, No Drawings

REDUCTION IN FALSE RESULTS IN ASSAY MEASUREMENTS

This application is a Divisional of U.S. patent application Ser. No. 12/823,953 filed Jun. 25, 2010, now U.S. Pat. No. 8,329,424.

BACKGROUND

The invention relates to methods and kits for the determination of the concentration of an analyte in a sample suspected of containing the analyte. More particularly, the invention relates to reducing false results in the measurements conducted during the above methods for the determination of the concentration of an analyte in a sample.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because the distribution and metabolism of an immunosuppressant drug can vary greatly between patients and because of the wide range and severity of adverse reactions, accurate monitoring of the drug level is essential.

In therapeutic drug monitoring field, selectively detecting the parent drug over its metabolites is often an important goal for designing immunoassays. This is especially true for immunosuppressant drugs. For that reason, HPLC tandem MS assays have become standard methods for the measurement of sirolimus, tacrolimus and other immunosuppressant drugs due to their ability to selectively measure the parent drug. However, the above methods are costly and time-consuming and are often employed to verify positive results obtained by another assay method rather than used in laboratories as an initial determination.

Most whole blood assays for immunosuppressant drugs require a manual step using reagents to extract the drug from blood constituents. As a result, the drug molecules and drug metabolite molecules are dissociated from endogenous binding proteins and are extracted into a relatively clean solution in which plasma proteins and lipoprotein particles as well as most other molecules are removed. Because precipitation techniques are usually used, the extracted sample is basically free of most blood macromolecules including drug-binding proteins. Thus, in the extracted samples, the parent drug and its metabolites are dissolved as unbound, individual molecules and compete with one another for reaction with an assay antibody in the immunoreaction mixture. The binding of assay antibody to the drug occurs in the absence of most endogenous substances in these assays. The cross-reactivity of a drug metabolite depends mostly on its antibody binding affinity in such assays.

In a homogeneous assay for an immunosuppressant drug where there is no manual extraction or separation of the drug from blood constituents, an antibody for the immunosuppressant drug has to detect the drug in the presence of most or all blood constituents, the presence of which might interfere with the binding of the antibody to the immunosuppressant drug and lead to a false assay result.

There is, therefore, a continuing need to develop fast and accurate diagnostic methods to measure levels of analytes in samples taken from a patient. The methods should be fully automatable and be accurate even when conducted on samples having various interfering substances. The assay should provide an accurate measurement of the amount of the analyte in the sample while minimizing inaccuracies resulting from interfering substances present in the sample. Reduction in false assay measurements is important to the accuracy of the methods.

SUMMARY

One embodiment of the present invention is a method for reducing false results in an assay measurement for determining a concentration of an analyte in a sample suspected of containing the analyte. The method comprises measuring assay signal resulting from background only and measuring assay signal resulting from the presence of analyte in the sample plus background and subtracting (a) from (b) to determine the concentration of analyte in the sample.

Another embodiment of the present invention is a method for reducing false results in an assay measurement for determining a concentration of an analyte in a sample suspected of containing the analyte. In the method measurement result 1 is determined by means of an assay conducted on the sample where analyte in the sample is substantially sequestered and measurement result 2 is determined by means of the assay conducted on the sample where analyte in the sample is substantially non-sequestered. Measurement result 1 is subtracted from measurement result 2 to determine the concentration of analyte in the sample.

Another embodiment of the present invention is a method for reducing false results in an assay measurement for determining a concentration of an analyte in a sample suspected of containing the analyte. Measurement result 1 is determined by means of an assay conducted on the sample where analyte in the sample is substantially sequestered. Measurement result 2 is determined by means of the assay conducted on the sample where analyte in the sample is substantially non-sequestered. The assay comprises adding reagents for determining the concentration of the analyte in the sample to a medium comprising the sample of measurement result 1 and to a medium comprising the sample of measurement result 2 wherein the reagents comprise at least one antibody for the analyte. An amount of a complex comprising the antibody for the analyte is measured for each assay. Measurement result 1 is subtracted from measurement result 2 to determine the concentration of analyte in the sample.

DETAILED DESCRIPTION OF SPECIFIC EMBODIMENTS

General Discussion

The present invention is directed to the accurate measurement of an analyte concentration in a sample by reducing or eliminating false assay results. In embodiments of the present methods, at least two assay measurements are carried out. The first measurement measures the level of signal generated only by the components of the sample other than the analyte, which bind to reagents employed in the assay either specifically or non-specifically. The second measurement measures the level of signal generated by the analyte and the other components of the sample, which bind to assay reagents. The difference between the two measurements represents the level of signal from analyte only and is thus representative of only the amount of analyte in the sample.

Embodiments of the present methods are directed to reducing false results in an assay measurement for determining a concentration of an analyte in a sample suspected of containing the analyte. A sample to be analyzed is obtained from a sample source and divided into portions. In the method, measurement result 1 is determined by means of an assay conducted on one portion of the sample where analyte in the sample is substantially sequestered and measurement result 2 is determined by means of the assay conducted on another portion of the sample of equal size where analyte in the sample is substantially non-sequestered. Measurement result 1 is subtracted from measurement result 2 to determine the concentration of analyte in the sample.

The sample to be tested may be non-biological or biological. "Non-biological samples" are those that do not relate to a biological material and include, for example, soil samples, water samples, air samples, samples of other gases and mineral samples. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid.

The analyte may be substantially sequestered as a result of one or more of the presence of components naturally occurring in the sample (which includes withholding a reagent from an assay medium that would otherwise assist in making analyte available for binding to a binding partner (thereby sequestering analyte signal) or the addition of a sequestering agent to the sample or a combination of the above. In the context of the present embodiments, "substantially sequestered" means that the analyte is at least 80%, or at least 90%, or at least 95%, or at least 99%, or at least 99.5%, or at least 99.9% or is 100% unavailable for detection during an assay. For example, the analyte may be unavailable for detection by a binding partner for the analyte that is employed for binding to the analyte to form an immune complex that serves as the basis for determining the amount of analyte in a sample.

Naturally-occurring sequestering agents are those components of a sample that are present in the sample as taken from a source, that is, the components are endogenous to the sample. The nature of the naturally-occurring sequestering agents is dependent on one or more of the nature of the sample, the nature of the source of the sample, the nature of the analyte, and the nature of the molecular complex comprising the analyte, for example. Naturally occurring sequestering agents include, by way of illustration and not limitation, lipophilic materials such as, for example, lipoproteins, lipid bilayer and plasma membranes; cells such as, for example, red blood cells; and proteins such as, for example, endogenous drug binding proteins such as, e.g., FKBP12, immunophilin, α1 acid glycoproteins, target of rapamycin (TOR), anti-analyte antibodies and receptors.

Sequestering agents that may be added to the sample are agents that are external to the sample and include naturally-occurring and synthetic materials. The nature of the sequestering agents that may be added is dependent on one or more of the nature of the sample, the nature of the source of the sample, the nature of the analyte, and the nature of the molecular complex that comprises the analyte, for example. The sequestering agent should not interfere with other reagents used in an assay such as, for example, binding partners and signal producing reagents; the external sequestering agent should not interfere with the generation of an assay signal. Naturally-occurring sequestering agents that may be added to the sample to sequester an analyte include, by way of illustration and not limitation, lipophilic materials such as, for example, lipoproteins, binding proteins such immunophilins, FK binding proteins and TOR; receptors such as, for example, protein receptors including, e.g., immunoglobulins, which includes antibodies (polyclonal and monoclonal, for example), protein A, anti-analyte antibodies and anti-analyte fragmented antibodies; synthetic constructs such as, for example, liposomes; lipoproteins such as, for example, chylomycrons, very low density lipoproteins, low density lipoproteins, intermediate density lipoproteins and high density lipoproteins; or a combination of two or more of the above. The amount of sequestering agent added to the sample is dependent on one or more of the nature of the sample, the nature of the source of the sample, the nature of the analyte, and the nature of the molecular complex that comprises the analyte, for example.

The amount of sequestering agent that is added to the sample is that which is sufficient to sequester the analyte so that the signal obtained in an assay on the sample is representative solely of components in the sample and not of analyte. In some embodiments the amount of sequestering agent is in the range (percents are by weight) of about 0.00001% to about 80%, or about 0.0001% to about 80%, or about 0.001% to about 80%, or about 0.01% to about 80%, or about 0.1% to about 80%, or about 1% to about 80%, or about 0.00001% to about 50%, or about 0.0001% to about 50%, or about 0.001% to about 50%, or about 0.01% to about 50%, or about 0.1% to about 50%, or about 1% to about 50%, or about 0.00001% to about 25%, or about 0.0001% to about 25%, or about 0.001% to about 25%, or about 0.01% to about 25%, or about 0.1% to about 25%, or about 1% to about 25%, or about 1% to about 30%, or about 0.00001% to about 1%, or about 0.001% to about 2%, or about 1% to about 30%, or about 5% to about 80%.

In some embodiments, non-sequestered analyte in sample portion 1 may be removed from the sample prior to conducting an assay on sample portion 1. Methods for removing or extracting the analyte from the sample include solvent extraction using, e.g., an organic solvent, or a combination of an organic solvent and water, for example.

In some embodiments analyte in a sample may be partially sequestered by naturally-occurring sequestering agents. In such embodiments, a sequestering agent that is external to the sample may be added so that the analyte becomes substantially sequestered. The amount of external sequestering agent that is added is an amount sufficient to sequester the non-sequestered analyte so that analyte in the sample is substantially sequestered and the signal obtained in an assay on the sample is representative of components in the sample and not of analyte.

In some embodiments analyte in a sample may be totally or partially sequestered by withdrawing an agent that otherwise might be added to assist in the measurement of analyte. In such embodiments, an analyte signal boosting agent that is external to the sample may be removed from the assay reagents so that the analyte becomes substantially sequestered. For example, the releasing reagent for the tacrolimus assay contains three major components to boost the assay signal. The first component is FK ester (FKE), which releases the drug from endogenous binding proteins. This agent can significantly boost the analyte signal because greater than 90% of the drug is protein bound and not accessible to the assay antibody. Releasing the drug from the binding proteins results in 7-fold signal increase. If FKE is removed from the pretreatment reagent, the analyte signal is substantially sequestered. The second component is a lysing agent such as, for example a detergent. The detergent makes the hydrophilic tacrolimus more water miscible in an aqueous assay mixture, thus rendering it more accessible by the assay measuring agents such as assay antibodies. If the detergents are removed from the reagent, drug molecules are less accessible to the assay antibody, which results in sequestered analyte signal. The third is a detergent that can prevent the drug from diffusing into lipoproteins particles or other type of liposomes. For example, PLURONIC® detergent is a detergent used in a tacrolimus assay to prevent the drug from diffusing into the core of lipoprotein complexes. Removing such detergent from the assay reagents enhances drug diffusion into lipoproteins, which results in substantially sequestered analyte signal.

The analyte is a substance of interest or the compound or composition to be detected and/or quantitated. Analytes include, by way of illustration and not limitation, therapeutic drugs, drugs of abuse, metabolites, pesticides, volatile organic compounds, semi-volatile organic compounds, non-volatile organic compounds, proteins, polysaccharides, pollutants, toxins, lipids and nucleic acids, (DNA, RNA), for example.

Representative drug analytes, by way of illustration and not limitation, include alkaloids, steroids, lactams, aminoalkylbenzenes, benzheterocyclics, purines, drugs derived from marijuana, hormones, polypeptides which includes proteins, immunosuppressants, vitamins, prostaglandins, tricyclic antidepressants, anti-neoplastics, nucleosides and nucleotides including polynucleosides and polynucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, and metabolites and derivatives of all of the above.

Also included within the term analyte are metabolites related to disease states, aminoglycosides, such as gentamicin, kanamicin, tobramycin, and amikacin, and pesticides such as, for example, polyhalogenated biphenyls, phosphate esters, thiophosphates, carbamates and polyhalogenated sulfenamides and their metabolites and derivatives.

The term analyte also includes combinations of two or more of polypeptides and proteins, polysaccharides and nucleic acids. Such combinations include, for example, components of bacteria, viruses, chromosomes, genes, mitochondria, nuclei and cell membranes. Protein analytes include, for example, immunoglobulins, cytokines, enzymes, hormones, cancer antigens, nutritional markers and tissue specific antigens. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides. As indicated above, the term analyte further includes oligonucleotide and polynucleotide analytes such as m-RNA, r-RNA, t-RNA, DNA and DNA-RNA duplexes, for example.

As referred to above, a portion of the same sample is employed for conducting assays to determine each of measurement results 1 and 2. For the measurements, the sample portion can be prepared in any convenient medium that does not interfere with an assay; an aqueous medium generally is employed. The size of the sample portion is dependent on one or more of the nature of the analyte, the nature of the assay, the nature of the various reagents for conducting the assay, and the nature of the complex comprising the analyte, for example. The size of the sample portion should be the same for both measurements. In some embodiments the volume of the sample portion is about 1 µL to about 100 µL, or about 2 µL to about 100 µL, or about 5 µL to about 100 µL, or about 10 µL about 100 µL, or about 1 µL to about 80 µL, or about 1 µL to about 60 µL, or about 1 µL to about 40 µL, or about 1 µL to about 20 µL, or about 5 µL to about 50 µL, or about 10 µL to about 50 µL, for example.

The portion of the sample for conducting an assay to obtain measurement result 1 is treated with a sequestering agent for the analyte if the analyte is not already substantially sequestered by one or more endogenous sequestering agents as discussed above. As mentioned above, the amount of sequestering agent that is added to the sample is that which is sufficient to sequester the analyte so that the signal obtained in an assay on the sample is representative solely of components in the sample and not of analyte. After addition of an external sequestering agent, the sample is incubated for a period of time under conditions to substantially sequester the analyte. The length and conditions of the incubation are dependent on one or more of the nature of the sequestering agent, the nature of the analyte, and the suspected concentration of the analyte, for example. In some embodiments incubation temperatures for this step may be about 5° to about 99°

C., or about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The incubation is usually carried out in a medium, which for convenience may be an assay medium as discussed herein, but need not be.

Following treatment, if necessary, of a first portion of the sample with a sequestering agent, the sample portion is subjected to an assay to determine measurement result 1. As discussed more fully below, any assay may be employed. The assay comprises adding reagents for determining the concentration of the analyte in the sample to a medium comprising the sample. In some embodiments the assay is an immunoassay and the reagents comprise at least one antibody for the analyte. An amount of a complex comprising the antibody for the analyte is measured. In this manner, the first measurement measures the level of signal generated only by components of the sample other than the analyte that bind to the antibody for the analyte to form a complex comprising the antibody for the analyte.

In accordance with present embodiments, a second portion of the sample is subjected to the same assay where analyte in the sample portion is substantially non-sequestered and an assay measurement result 2 is determined. In some embodiments depending on the nature of the sample and the analyte, one or more releasing agents are added to the sample to release the analyte from any endogenous binding substances present in the sample. The nature of the releasing agents is dependent on one or more of the nature of the analyte, the nature of the sample, the nature of the endogenous binding substances in the sample, and the nature of analyte binding materials such as, e.g., analyte binding proteins, for example. The releasing agent can, and does in many instances, displace analyte and metabolites of the analyte from endogenous binding moieties. In some embodiments the releasing agent has high binding affinity to endogenous binding proteins so that it readily displaces the analyte and, in some instances, its metabolites, from endogenous binding proteins. In addition, the releasing agent does not bind to any significant degree to an antibody for the analyte that is used in the assay. By the phrase "does not bind to any significant degree" is meant that the extent of binding should be low enough so that an accurate assay for the analyte may be carried out.

The releasing agent may be any moiety, either a single compound or a mixture of compounds, which accomplishes the desired result of displacement with no significant binding to assay reagents such as, for example, an assay antibody. In some embodiments the releasing agent displaces the analyte, and its metabolites if required, from endogenous binding substances to render both the analyte and the metabolites substantially equally accessible to a binding partner for the analyte such as, for example, an antibody for the analyte. The amount of metabolites available for binding to an antibody for the analyte is dependent on considerations such as, for example, the binding affinity of particular metabolites for the antibody for the analyte.

In some embodiments the releasing agent is an analog, including structural analogs, of the analyte. An analyte analog is a modified analyte that can displace the analogous analyte from a binding protein but does not compete to any substantial degree for a receptor such as an antibody for the analyte. The modification provides means to join an analyte analog to another molecule. The analyte analog will usually differ from the analyte by more than replacement of a hydrogen with a bond which links the analyte analog to a hub or label, but need not. The analyte analog may be, for example, the analyte conjugated to another molecule through a linking group, and so forth. For analytes that comprise a hydroxyl or carboxylic acid functionality, the releasing agent may be an ester of the analyte, which has a high binding affinity for endogenous binding proteins relative to the analyte to be detected and which has no significant binding affinity for an antibody for the analyte. A structural analog is a moiety that has the same or similar structural or spatial characteristics as the analyte such that the structural analog accomplishes the same or similar result as the analog of the analyte. The structural analog may be, for example, another compound that is related to the analyte.

In some embodiments the releasing agent may be an agent that disrupts cellular membranes in which the analyte is entrapped. For example, an analyte that is entrapped within red blood cells may be released from the red blood cells by employing a hemolytic agent. A hemolytic agent is a compound or mixture of compounds that disrupt the integrity of the membranes of red blood cells thereby releasing intracellular contents of the cells and, in particular, erythrocytes. Numerous hemolytic agents are known in the art. Hemolytic agents include, for example, non-ionic detergents, anionic detergents, amphoteric detergents, low ionic strength aqueous solutions (hypotonic solutions), bacterial agents, antibodies that cause complement dependent lysis, and the like. Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis(ethoxylate-block-propoxylate) tetrol, IGEPAL®, MERPOL®, poly(ethylene glycol), 2-[ethyl[(heptadecafluorooctyl)sulfonyl]amino]ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanolamine, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

Other releasing agents that may be employed in the present embodiments include solubility reagents such as, for example, a small amount of an organic solvent such as, e.g., methanol, ethanol, isopropanol, methoxy propanol and DMSO; and agents for carrying out protein digestion such as, for example, proteinases, trypsin, pepsin, peptidases; for example.

The concentration of the releasing agent in the medium is that sufficient to achieve the desired result of releasing the analyte, and in some instances metabolites of the analyte, from endogenous binding moieties to render the analyte, and metabolites, accessible for binding to an antibody for the analyte as discussed above. The analyte thereby becomes substantially non-sequestered. In the context of the present embodiments, "substantially non-sequestered" means that the analyte is at least 80%, or at least 90%, or at least 95%, or at least 99%, or at least 99.5%, or at least 99.9% or is 100% available for detection during an assay. The amount or concentration of the releasing agent employed depends on one or more of the nature of the sample, the nature of the analyte, the nature of analyte metabolites, the nature of other reagent components, and the reaction conditions, for example. In some embodiments the amount of the releasing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume).

After addition of a releasing agent, the second sample portion is incubated for a period of time under conditions to substantially release the analyte. The length and conditions of the incubation are dependent on one or more of the nature of the releasing agent, the nature of the analyte, the suspected concentration of the analyte, the antibody affinity and avidity and antibody fragmentation, for example. In some embodiments incubation temperatures for this step may be about 5° to about 99° C., or about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The incubation is usually carried out in a medium, which for convenience may be an assay medium as discussed herein, but need not be.

Following treatment, if necessary, of a second portion of the sample with a releasing agent, the sample portion is subjected to the same assay as that for the first portion of the sample to determine an assay measurement result 2. As discussed more fully below, any assay may be employed. The assay comprises adding reagents for determining the concentration of the analyte in the sample to a medium comprising the sample. For immunoassays, the reagents comprise at least one antibody for the analyte. An amount of a complex comprising the antibody for the analyte is measured and the amount of the complex is related to the concentration of the analyte and other substances in the sample. In this manner the second measurement measures the level of signal generated by the analyte and other components of the sample, which, for example, bind to the antibody for the analyte to form a complex comprising the antibody for the analyte. Accordingly, the phrase "complex comprising the antibody for the analyte" refers to a complex wherein the antibody for the analyte is complexed to one or more substances that may be one or more of the analyte and other substances in a sample that bind to the antibody for the analyte.

The assays conducted on the first and second sample portions may be carried out sequentially or concomitantly in separate reaction vessels or sequentially in the same reaction vessel.

Following the assays conducted on the first and second sample portions to obtain measurement result 1 and measurement result 2, respectively, measurement result 1 is subtracted from measurement result 2 to determine the concentration of analyte in the sample, which is representative of the concentration of only the analyte in the sample. The difference between the two measurements, therefore, represents the level of signal from analyte only.

General Description of Assays for an Analyte

Any suitable assay may be employed for determining assay measurement result 1 and assay measurement result 2 as discussed above. The assays may be conducted on the sample portions as an immediate continuation of the treatment of the portions as discussed above or the assay may be carried out at a point thereafter. The assays are conducted by combining the respective sample portions with reagents for determining the amount of the analyte in the sample. The nature of the reagents is dependent on the particular type of assay to be performed. In general, the assay is a method for the determination of the amount of an analyte in a sample. The assay may be an immunoassay or a non-immunoassay. Various assay methods are discussed below by way of illustration and not limitation.

In many embodiments the reagents comprise at least one antibody for the analyte and the assay is generally referred to as an immunoassay as distinguished from assays that do not utilize an antibody, which are referred to as non-immunoassays. By the phrase "antibody for the analyte" is meant an antibody that binds specifically to the analyte (and to closely related structural analogs of the analyte such as metabolites of the analyte) and does not bind to any significant degree to other substances that would distort the analysis for the analyte.

One general group of immunoassays that may be employed includes immunoassays using a limited concentration of antibody. Another group of immunoassays involves the use of an excess of one or more of the principal reagents such as, for example, an excess of an antibody for the analyte. Another group of immunoassays are separation-free homogeneous assays in which the labeled reagents modulate the label signal upon analyte-antibody binding reactions. Another group of assays includes labeled antibody reagent limited competitive assays for analyte that avoid the use of problematic labeled haptens. In this type of assay, a solid phase immobilized analyte is present in a constant, limited amount. The partition of a label between the immobilized analyte and free analyte depends on the concentration of analyte in the sample.

Antibodies specific for an analyte for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG 1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

As discussed above, an antibody selected for use in an immunoassay for an analyte, for example, should specifically and preferentially bind the analyte (and its pharmaceutically active metabolites, if necessary or desired) over other ligands such as other metabolites or related substances.

Other reagents are included in the assay medium depending on the nature of the assay to be conducted. Such assays usually involve reactions between binding partners such as an analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as, for example, biotin-avidin, hormones-hormone receptors, enzyme-substrate, nucleic acid duplexes, IgG-protein A, and polynucleotide pairs such as DNA-DNA, DNA-RNA, are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. In many embodiments of assays, preferred binding partners are antibodies and the assays are referred to as immunoassays.

The immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include enzyme immunoassays, fluorescence polarization immunoassays, radioimmunoassay, inhibition assay, induced luminescence, fluorescent oxygen channeling assay, and so forth.

In some embodiments homogeneous immunoassays may be employed; such assays may also be referred to as essentially partition-free immunoassays. The present methods have application to fully automated homogeneous assays in which, prior to the assay, there is no extraction or separation of the analyte from other constituents of the sample including analyte metabolites. In a "non-manual extraction" assay, a sample such as a whole blood sample, without extraction in, e.g., an organic solvent, is combined with reagents for conducting an assay for the analyte in a suitable medium and the assay method is conducted. The present methods also find application to manual extraction assays.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); acridinium ester label immunoassays using paramagnetic particles as a solid phase (ADVIA Centaur immunoassays); and so forth. Other types of assays include immunosensor assays involving the monitoring of the changes in the optical, acoustic and electrical properties of an antibody-immobilized surface upon the binding of a hydrophobic drug. Such assays include, for example, optical immunosensor assays, acoustic immunosensor assays, semiconductor immunosensor assays, electrochemical transducer immunosensor assays, potentiometric immunosensor assays, amperometric electrode assays, and the like.

In many of the assays discussed herein for determination of an analyte, a label is employed; the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the analyte being detected or to an agent that reflects the amount of the analyte to be detected. The label is any molecule that produces or can be induced to produce a signal, and may be, for example, a fluorescer, radiolabel, enzyme, chemiluminescer or photosensitizer. Thus, the signal is detected and/or measured by detecting enzyme activity, luminescence, light absorbance or radioactivity, and so forth, as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol and acridinium esters, for example; sensitizers; coenzymes; enzyme substrates; radiolabels such as $^{125}$I, $^{131}$I, $^{14}$C, $^{3}$H, $^{57}$Co and $^{75}$Se; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members can be bound to a support. An erythrocytophilic drug derivative or analog may be bound to a solid support in any manner known in the art, provided only that the binding does not substantially interfere with the analogs ability to bind with an antibody. In some embodiments, the erythrocytophilic drug derivative or analog may be coated or covalently bound directly to the solid phase or may have layers of one or more carrier molecules such as poly (amino acids) including proteins such as serum albumins or immunoglobulins, or polysaccharides (carbohydrates) such as, for example, dextran or dextran derivatives. Linking groups may also be used to covalently couple the solid support and the erythrocytophilic drug. Other methods of binding the erythrocytophilic drug derivatives are also possible. For instance, a solid support may have a coating of a binder for a small molecule such as, for example, avidin, an antibody, etc., and a small molecule such as, e.g., biotin, hapten, etc., can be bound to the erythrocytophilic drug derivative or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, paper, etc., fiber, and the like. Depending on the type of assay, the support may or may not be suspendable in the medium in which it is employed. Examples of suspendable supports are polymeric materials such as latex, lipid bilayers or liposomes, oil droplets, cells and hydrogels, magnetic particles, and the like. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus*, *Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chromium dioxide (chrome) particles or latex particles.

The polymer particles can be formed of addition or condensation polymers. The particles will be readily dispersible in an aqueous medium and can be adsorptive or functionalizable so as to permit conjugation to an erythrocytophilic drug analog, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The label and/or other sps member may be bound to an sbp member or another molecule. For example, the label can be bound covalently to an sbp member such as, for example, an antibody, a receptor for an antibody, a receptor that is capable of binding to a small molecule conjugated to an antibody, or a ligand (analyte) analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

With label proteins such as, for example, enzymes, the molecular weight range will be from about 10,000 to about 600,000, or from about 10,000 to about 300,000 molecular weight. There is usually at least about 1 erythrocytophilic drug analog per about 200,000 molecular weight, or at least about 1 per about 150,000 molecular weight, or at least about 1 per about 100,000 molecular weight, or at least about 1 per about 50,000 molecular weight, for example. In the case of enzymes, the number of erythrocytophilic drug analog groups is from 1 to about 20, about 2 to about 15, about 3 to about 12, or about 6 to about 10, for example.

The term "non-poly(amino acid) labels" includes those labels that are not proteins (e.g., enzymes). The non-poly (amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the non-poly(amino acid) label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle or the like, metal sol, crystallite, liposome, cell, etc., which may or may not be further labeled with a dye, catalyst or other detectable group, and the like.

In one embodiment the assay is an induced luminescence immunoassay, which is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member, for example, an antibody for the analyte that is capable of binding to the analyte to form a complex, or to a second sbp member to form a complex, in relation to the amount of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which comprises antibody for the analyte.

By way of further illustration, chemiluminescent particles are employed, which comprise the chemiluminescent compound associated therewith such as by incorporation therein or attachment thereto. An sbp member that binds to the analyte, such as, for example, an antibody for analyte, is bound to a polysaccharide coating the particles. A second sbp member that binds to the analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with the respective portion of the sample suspected of containing an analyte and with the photosensitizer particles. With regard to the first portion of the sample, the reaction medium is incubated to allow the particles to bind to substances or components in the sample other than analyte. With regard to the second portion of the sample, the reaction medium is incubated to allow the particles to bind to the analyte by virtue of the binding of the sbp members to the analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the substances and/or the analyte, it is activated by singlet oxygen and emits luminescence. The medium is then examined for the amount of luminescence or light emitted, the presence thereof being related to the amount of the substances that bind to antibody for the analyte or the amount of analyte.

Another particular example of an assay that may be employed for the determination of an analyte is discussed in U.S. Pat. No. 5,616,719 (Davalian, et al.), which describes fluorescent oxygen channeling immunoassays.

The assays discussed above are normally carried out in an aqueous buffered medium at a moderate pH, generally that which provides optimum assay sensitivity. The pH for the assay medium will usually be in the range of about 4 to about 11, or in the range of about 5 to about 10, or in the range of about 6.5 to about 9.5. The pH will usually be a compromise between optimum binding of the binding members of any specific binding pairs, the pH optimum for other reagents of the assay such as members of a signal producing system, and so forth.

Various buffers may be used to achieve the desired pH and maintain the pH during the determination. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. In some embodiments, in addition to these additives, proteins may be included, such as albumins; quaternary ammonium salts; polyanions such as dextran sulfate; binding enhancers, or the like. All of the above materials are present in a concentration or amount sufficient to achieve the desired effect or function.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., or from about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents. Temperatures during measurements will generally range from about 10 to about 50° C., or from about 15 to about 40° C.

The concentration of analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of erythrocytophilic drug analyte present in the sample), the particular detection technique and the concentration of the analyte normally determine the concentrations of the various reagents.

The concentrations of the various reagents in the assay medium will generally be determined by the concentration range of interest of the analyte, the nature of the assay, the antibody affinity and avidity and antibody fragmentation, for example. However, the final concentration of each of the reagents is normally determined empirically to optimize the sensitivity of the assay over the range. That is, a variation in concentration of analyte that is of significance should provide an accurately measurable signal difference. Considerations such as the nature of a signal producing system and the nature of the analyte normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as cussed above.

Measurement Step

The methods of the present embodiments wherein an immunoassay is used comprise examining each respective assay medium for the amount of a complex comprising the antibody for the analyte (anti-analyte antibody). The measurement is carried out respectively for each assay medium following the incubation of the assay medium in accordance with the particular assay employed. In the case of sample portion 1, the measurement reflects binding of substances other than the analyte to anti-analyte antibody to form a complex comprising the anti-analyte antibody. In the case of sample portion 2, the measurement reflects binding of analyte and substances other than analyte to anti-analyte antibody to form a complex comprising the anti-analyte antibody. Subtraction of measurement result 1 from measurement result 2 gives the amount of the analyte in the sample.

The phrase "measuring the amount of an analyte" refers to the quantitative, semi-quantitative and qualitative determination of the analyte. Methods that are quantitative, semi-quantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the present embodiments. The terms "detecting" and "determining," as well as other common synonyms for measuring, are contemplated within the scope of the present embodiments.

In many embodiments the examination of the medium involves detection of a signal from the medium. The amount of the signal is related to the amount of the analyte in the sample. The particular mode of detection depends on the nature of the signal producing system. As discussed herein, there are numerous methods by which a label of an sps can produce a signal detectable by external means, desirably by visual examination, and include, for example, electromagnetic radiation, electrochemistry, heat, radioactivity detection, chemical reagents and so forth.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems, addition of a substrate and/or a cofactor may be necessary.

The examination for amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, or a photographic instrument, for example. The amount of signal detected is related to the amount of the analyte present in a sample. Temperatures during measurements generally range from about 10° to about 70° C., or from about 20° to about 45° C., or about 20° to about 25° C., for example. In one approach standard curves are formed using known concentrations of the analytes to be screened. As discussed herein, calibrators and other controls may also be used.

Specific Embodiment of an Immunoassay for Determination of an Erythrocytophilic Drug In one embodiment, by way of illustration and not limitation, the analyte is an erythrocytophilic drug. The term "erythrocytophilic drug" as used herein refers to a drug, usually a therapeutic drug, where the drug exhibits a characteristic of absorption by an erythrocyte. The erythrocytophilic drug is usually hydrophobic and exhibits a characteristic of absorption by a lipophilic moiety such as, for example, a lipoprotein, e.g., an erythrocyte, or a drug-specific binding protein, or of reduced solubility in a polar medium. The absorption of the drug by an erythrocyte is at least about 70%, or at least about 75%, or at least about 80%, or at least about 85%, or at least about 90%, or at least about 95%, or at least about 96%, or at least about 97%, or at least about 98%, or at least about 99%, for example. Accordingly, an erythrocytophilic drug is sequestered by one or more naturally-occurring sequestering agents, namely, lipophilic moieties endogenous in the sample containing the erythrocytophilic drug to the extent the drug is absorbed by, for example, an erythrocyte.

Immunosuppressant drugs are an example of erythrocytophilic drugs and are also considered as hydrophobic drugs. Immunosuppressant drugs are therapeutic drugs that are administered to transplant recipients in order to help prevent allograft rejection of non-self tissue. Immunosuppressive drugs can be classified as follows: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins, the latter of which specifically bind, for example, tacrolimus or sirolimus. The immunosuppressant drugs that act on immunophilin include, for example, cyclosporin (including cyclosporin A, cyclosporin B, cyclosporin C, cyclosporin D, cyclosporin E, cyclosporin F, cyclosporin G, cyclosporin H, cyclosporin I), tacrolimus (FK506, PROGRAF®), sirolimus (rapamycin, RAPAMUNE®), everolimus (RAD, CERTICAN®) and so forth.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

In the above embodiment, the sample to be analyzed is one that is suspected of containing one or more erythrocytophilic drug analytes. The sample typically comprises one or more naturally-occurring sequestering agents that bind to the erythrocytophilic drug. As mentioned above, naturally-occurring sequestering agents for the erythrocytophilic drug may be binding proteins that bind a hydrophobic drug such as a lipoprotein, e.g., a protein that comprises a hydrophobic cavity on the surface or other spatial features that bind the hydrophobic drug such as, for example, cholesterol and triglyceride. In this exemplary embodiment, the sample is whole blood, which is unfractionated blood or blood that comprises both red cells and plasma. In accordance with present embodiments, in this example equal portions, portion 1 and portion 2, are subjected to the assay method chosen.

In conducting an assay to determine measurement result 1 in accordance with an embodiment of the present methods, sample portion 1 is not pretreated to remove naturally-occurring sequestering agents. Moreover, where the erythrocytophilic drug is only partially sequestered but not substantially sequestered by one or more naturally-occurring sequestering agents in the sample, an external sequestering agent can be added for conducting an assay to obtain measurement result 1 in an amount sufficient to substantially sequester the erythrocytophilic drug. In one embodiment the external sequestering agent is an antibody for the erythrocytophilic drug that binds to the drug but does not bind to interfering substances in the sample and does not interfere with any of the reagents for conducting the assay including antibody for the analyte. The assay is conducted on sample portion 1 of the whole blood sample to determine measurement result 1.

For sample portion 2, where the whole blood sample comprises naturally-occurring sequestering agents or endogenous binding materials for the erythrocytophilic drug such as, for example, lipoproteins or other naturally-occurring sequestering agents, sample portion 2 is treated with one or more releasing agents to release analyte from such endogenous substances. For the erythrocytophilic drug in this example, the releasing agents include at least a hemolytic agent as discussed above to release the erythrocytophilic drug from red blood cells. The nature and amount or concentration of hemolytic agent employed is discussed above.

In some embodiments the releasing agent(s) for sample portion 2 include an analog, including structural analogs, of the erythrocytophilic drug. An erythrocytophilic drug analog is a modified drug that can displace the analogous erythrocytophilic drug from a binding protein but does not compete to any substantial degree for an antibody for the erythrocytophilic drug. For example, in a determination for tacrolimus, an ester of tacrolimus (e.g., FK506) may be employed as the releasing agent so long as it meets the above requirements. In the case of an erythrocytophilic drug, the structural analog may be, for example, another compound that is related to the erythrocytophilic drug. For example, in a determination for sirolimus, an ester of tacrolimus may be employed as the releasing agent. The ester may be, for example, a carbamate, a carbonate, an ester of a $C_1$ to $C_6$ carboxylic acid, and the like. See, for example, U.S. Pat. No. 7,186,518, the relevant disclosure of which is incorporated herein by reference. Other examples of releasing agents include [$Thr_2$, $Leu_5$, $D-Hiv_8$, $Leu_{10}$]-cyclosporin A for cyclosporin A, FK506 for sirolimus, sirolimus for FK506, and the like. See, for example, U.S. Pat. No. 6,187,547, the relevant disclosure of which is incorporated herein by reference. The concentration of the releasing agent in the medium is that sufficient to achieve the desired result of displacing substantially all of the erythrocytophilic drug, and in many instances metabolites of the erythrocytophilic drug, from endogenous binding moieties to render the drug and metabolites accessible for binding to an antibody for the drug as discussed above. By the term "substantially all" is meant that the at least about 80%, or at least about 90%, or at least about 95%, or at least about 99%, or at least 99.5%, or at least 99.9%, or 100% of the drug in the sample is available for binding to a receptor for the drug.

In some embodiments sample portion 2, a hemolytic agent and an additional releasing agent (if employed) are combined in a medium, which, as mentioned above, is usually an aqueous medium. All of the above may be combined simultaneously in the medium or one or more of the above reagents may be added sequentially in concentrations as discussed above. The medium may also comprise one or more preservatives as are known in the art such as, for example, sodium azide, neomycin sulfate, PROCLIN® 300, Streptomycin, and the like.

The pH for the medium will usually be in the range of about 4 to about 11, more usually in the range of about 5 to about 10, and preferably in the range of about 6.5 to about 9.5. As discussed above, various buffers may be used to achieve the desired pH and maintain the pH during the incubation period. Illustrative buffers include borate, phosphate, carbonate, tris, barbital, PIPES, HEPES, MES, ACES, MOPS, BICINE, and the like. The medium may also comprise agents for preventing the formation of blood clots. Such agents are well known in the art and include, for example, EDTA, EGTA, citrate, heparin, and the like. Various ancillary materials may be employed in the above methods. For example, in addition to buffers and preservatives, the medium may comprise stabilizers for the medium and for the reagents employed. All of the above materials are present in a concentration or amount sufficient to achieve the desired effect or function.

The medium is incubated under conditions for hemolyzing cells in the sample and for releasing the erythrocytophilic drug and its metabolites from endogenous binding moieties. The incubation period may be about 1 second to about 60 minutes, or about 1 second to about 6 minutes, or about 1 second to about 5 minutes, or about 1 second to about 3 minutes, or about 1 second to about 2 minutes, or about 1 second to about 1 minute, or about 1 second to about 30 seconds, or about 1 second to about 20 seconds, or about 1 second to about 10 seconds, or about 5 seconds to about 60 minutes, or about 5 seconds to about 6 minutes, or about 5 seconds to about 5 minutes, or about 5 seconds to about 3 minutes, or about 5 seconds to about 2 minutes, or about 5 seconds to about 1 minute, or about 5 seconds to about 30 seconds, or about 5 seconds to about 20 seconds, or about 5 seconds to about 10 seconds, for example.

The temperature during the incubation is usually about 10° C. to about 45° C., or about 10° C. to about 35° C., or about 10° C. to about 25° C., or about 15° C. to about 45° C., or about 15° C. to about 35° C., or about 15° C. to about 25° C., or about 20° C. to about 45° C., or about 20° C. to about 35° C., or about 20° C. to about 25° C., for example.

Following the above treatment, sample portion 2 is subjected to the same assay as that for sample portion 1 to determine measurement result 2. Any suitable assay may be employed for determining the concentration of analyte in sample portion 1 and sample portion 2. The assays may be conducted on the sample portions as an immediate continuation of the pretreatment of the portions or the assay may be carried out at a point thereafter. The assays are conducted by combining the respective sample portions with reagents for determining the amount of the erythrocytophilic drug in the sample in an assay medium. The nature of the reagents is dependent on the particular type of assay to be performed. In general, the assay is a method for the determination or measuring of the amount of an erythrocytophilic analyte. Various assay methods are discussed herein by way of illustration and not limitation. In many embodiments the reagents comprise at least one antibody for the erythrocytophilic drug.

As discussed above, an antibody selected for use in an immunoassay for an erythrocytophilic drug, for example, should specifically and preferentially bind the erythrocytophilic drug and its pharmaceutically active metabolites over other ligands such as other metabolites or related drugs. For example, an antibody for tacrolimus should specifically and preferentially bind tacrolimus over, e.g., rapamycin. In general, an antibody should be capable of distinguishing between one erythrocytophilic drug relative to a second erythrocytophilic drug. At least about 5-fold, at least about 10-fold, or at least about 20-fold, of the first erythrocytophilic drug will be bound to the antibody if the antibody is combined with a sample containing the erythrocytophilic drug. While the binding also depends on relative concentration of the erythrocytophilic drug, the binding will be higher for the first erythrocytophilic drug if the binding constant for the first erythrocytophilic drug is greater than the binding constant for the second erythrocytophilic drug, at least about 10-fold higher or at least about 50-fold higher and up to 1000-fold or higher. Other reagents are included in the assay medium depending on the nature of the assay to be conducted. Such assays usually involve reactions between binding partners such as an erythrocytophilic drug analyte and a corresponding antibody or the binding between an antibody and a corresponding binding partner such as a second antibody that binds to the first antibody.

Following the assays on sample portions 1 and 2, the medium is examined for the presence of a complex comprising the antibody for the erythrocytophilic drug. The subtraction of the amount of the complex obtained using sample portion 1 from the amount obtained using sample portion 2 provides the amount of the erythrocytophilic drug in the sample.

In many embodiments the examination of the medium involves detection of a signal from the medium. Depending on which sample portion is being examined, the amount of the signal is related to the amount of components in the sample other than erythrocytophilic drug that bind to the antibody for the erythrocytophilic drug or to the amount of such components plus the erythrocytophilic drug in the sample. The particular mode of detection depends on the nature of the sps. As discussed above, there are numerous methods by which a label of an sps can produce a signal detectable by external means, desirably by visual examination, and include, for example, electromagnetic radiation, electrochemistry, heat, radioactivity detection, chemical reagents and so forth.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems, addition of a substrate and/or a cofactor may be necessary.

The examination for amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The amount of signal detected is related to the amount of the hydrophobic drug compound present in a sample if the assay is making an accurate determination. Temperatures during measurements generally range from about 10° to about 70° C., or from about 20° to about 45° C., or about 20° to about 25° C., for example. In one approach standard curves are formed using known concentrations of the analytes to be screened. As discussed herein, calibrators and other controls may also be used.

Specific Embodiments of Assays for Certain Erythrocytophilic Analytes

Specific embodiments of assays that may be employed to assay the respective sample portions are discussed next by way of illustration and not limitation.

In a homogeneous assay, after all of the reagents have been combined, the signal is determined and related to the amount of analyte in the sample. For example, in an EMIT® assay for an analyte, a sample suspected of containing the analyte is combined in an aqueous medium either simultaneously or sequentially with an enzyme conjugate of the analyte, i.e., an analog of the analyte, and antibody capable of recognizing the analyte. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The analyte (and/or other substances in the sample that might bind to the antibody) and the moieties of the enzyme conjugate compete for binding sites on the antibody. The enzyme activity in the medium is then measured, usually by spectrophotometric means. Calibrators may also be tested in a manner similar to the testing of the sample suspected of containing the analyte. The calibrators typically contain differing, but known, concentrations of the analyte to be determined. Preferably, the concentration ranges present in the calibrators span the range of suspected analyte concentrations in unknown samples.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using antibodies for the analyte and using procedures as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, which disclosure is incorporated herein by reference. In one type of competitive assay, a support, as discussed herein, having antibodies for the analyte bound thereto is contacted with a medium containing the sample and appropriate enzyme conjugates of the analyte. After separating the support and the medium, the enzyme activity of the support or the medium is determined by conventional techniques to determine the measurement result.

In certain embodiments a second enzyme may be employed in addition to the enzyme of the enzyme conjugate. The enzymes of the pair of enzymes are related in that a product of the first enzyme serves as a substrate for the second enzyme.

Another embodiment of an assay format is a capture assay. In this assay format, the antibody for the analyte is covalently bound to a magnetic particle. The sample is incubated with these particles to allow the antibodies for the analyte to bind to the analyte and/or substances in the sample other than analyte that also bind to the antibody. Subsequently, an enzyme that has the analyte or a derivative of the analyte covalently attached is incubated with the magnetic particles. After washing, the amount of enzyme that is bound to the magnetic particles is measured and is inversely related to the amount of a complex comprising the antibody for the analyte.

The following specific assay descriptions are by way of illustration of, and not as a limitation on, the scope of the present invention. Selection of tacrolimus or sirolimus as the erythrocytophilic drug is also by way of illustration and not limitation as the present invention has general application to detection of erythrocytophilic drugs in general and immunosuppressant drugs in particular.

In one embodiment, the sample portion is mixed with a tacrolimus conjugate, i.e., for example, an analog of tacrolimus that is attached to biotin. Depending on the portion of the sample being analyzed, the sample portion is incubated to allow binding of substances in the sample other than analyte to bind to an antibody for tacrolimus or to allow binding of such substances and the tacrolimus of the sample to bind to the antibody for tacrolimus in competition with the analog of tacrolimus where the antibody is capable of binding to tacrolimus or the analog of tacrolimus. After rinsing with an appropriate wash buffer, a detection molecule consisting of streptavidin or avidin conjugated to an enzyme, florescent or chemiluminescent molecule or radioactive moiety can be added to the medium, which is then examined for the amount of signal. The amount of signal is related to the amount of the substances other than tacrolimus in the sample that bind to antibody for tacrolimus or to the amount of such substances and tacrolimus in the sample.

In one embodiment the assay employed is an induced luminescence assay as described above. In some embodiments of the induced luminescence assay by way of illustration and not limitation, the reagents include two latex bead reagents and a biotinylated anti-tacrolimus mouse monoclonal antibody. The first bead reagent is coated with tacrolimus or a tacrolimus analog and contains chemiluminescent dye. The second bead reagent is coated with streptavidin and contains a photosensitizer dye. A sample suspected of containing tacrolimus is divided into equal portions, namely, sample portion 1 and sample portion 2. Sample portion 1 is treated with an antibody for tacrolimus to substantially sequester any non-sequestered tacrolimus. Sample portion 1 is incubated with biotinylated antibody for tacrolimus, which allows substances in the sample other than tacrolimus to saturate a fraction of the biotinylated antibody. In a second step, the first bead reagent is added and leads to the formation of bead/biotinylated antibody immunocomplexes with the non-saturated fraction of the biotinylated antibody. The second bead reagent is then added and binds to the biotin to form bead pair immunocomplexes. When illuminated by light at 680 nm, the second bead reagent converts dissolved oxygen in the reaction solution into the more energetic singlet oxygen form. In the bead pairs, the singlet oxygen diffuses into the first bead reagent thereby triggering a chemiluminescent reaction. The resulting chemiluminescent signal is measured at 612 nm and is an inverse function of the concentration of the substances other that tacrolimus in the sample that bind to tacrolimus antibody. The amount of this signal is related to the amount of such substances in the sample.

The same assay is also carried out on sample portion 2, which is treated with FK506 to release tacrolimus from endogenous binding substances in the sample. After conducting the assay, the resulting chemiluminescent signal is measured at 612 nm and is an inverse function of the concentration of both tacrolimus and the substances other that tacrolimus in the sample that bind to tacrolimus antibody. Subtraction of the signal obtained from sample portion 1 from the signal obtained from sample portion 2 gives the amount of signal attributed to the amount of tacrolimus in the sample.

A specific example of another assay format is ACMIA (Affinity Chromium dioxide Mediated Immuno Assay). For the ACMIA assay format, chrome particles, which are coated with sirolimus or a sirolimus analog, are employed as a first component. A second component is an antibody for sirolimus. This antibody, crosslinked to a reporter enzyme (for example, beta-galactosidase), is added to a reaction vessel in an excess amount, i.e., an amount greater than that required to bind all of the analyte that might be present in a sample. A sample suspected of containing sirolimus is divided into equal portions, namely, sample portion 1 and sample portion 2. Sample portion 1 is treated with an antibody for sirolimus, which binds to sirolimus but not to other reagents employed in the assay or to interfering substances in the sample, to substantially sequester sirolimus. The antibody-enzyme conjugate is mixed with sample portion 1 to allow the sirolimus analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of substances in the sample, other than sirolimus, which bind to antibody for sirolimus.

The same assay is also carried out on sample portion 2, which is treated with a tacrolimus ester to release sirolimus from endogenous binding substances in the sample. After conducting the assay, the resulting enzyme activity is measured and is related to the amount of both sirolimus and the substances other that sirolimus in the sample that bind to sirolimus antibody. Subtraction of the enzyme activity obtained from sample portion 1 from the enzyme activity obtained from sample portion 2 gives the amount of enzyme activity attributed to the amount of sirolimus in the sample.

In a sandwich assay format, a first reagent comprising chrome particles coated with anti-tacrolimus antibodies and a second reagent comprising a second antibody (or binding protein) for the first antibody conjugated to a reporter enzyme are employed. A sample suspected of containing tacrolimus is divided into equal portions, namely, sample portion 1 and sample portion 2. Sample portion 1 is treated with antibody for tacrolimus to substantially sequester any non-sequestered tacrolimus. In this format, sample portion 1 is incubated with the chrome particles so that all of the tacrolimus, if present in the sample, becomes bound to the chrome particles. The chrome particles are washed, using a magnet to separate the bound analyte from the supernatant. Then, the second reagent, i.e., antibody (or binding protein) conjugated to a reporter enzyme, is incubated with the chrome particles to form a "sandwich". After washing, the amount of enzyme that is bound to the chrome is measured and is related to the amount of substances in sample portion 1, other than tacrolimus, which bind to antibody for tacrolimus. The same assay is also carried out on sample portion 2, which is treated with FK506 ester to release tacrolimus from endogenous binding substances in the sample. After conducting the assay, the amount of enzyme that is bound to the chrome is measured and is related to the amount of both tacrolimus and the substances other that tacrolimus in the sample that bind to tacrolimus antibody. Subtraction of the amount of enzyme bound to the chrome obtained from sample portion 1 from the amount of enzyme bound to chrome obtained from sample portion 2 gives the amount of enzyme bound to chrome attributed to the amount of tacrolimus in the sample.

Another assay format is EMIT® (Enzyme-Mediated Immunoassay Technology). A sample suspected of containing sirolimus is divided into equal portions, namely, sample portion 1 and sample portion 2. Sample portion 1 is treated with excess amount of analyte binding proteins or anti-analyte antibodies that do not recognize the drug analog conjugated with G-6-PDH to substantially sequester sirolimus. In this assay format, an enzyme conjugate is formed such as, for example, a conjugate of G-6-PDH and a sirolimus analog. An antibody for sirolimus is incubated with the enzyme-conjugate and sample portion 1. Antibody for sirolimus binds to substances other than sirolimus in the sample instead of binding to the enzyme conjugate, which reduces the amount of inhibition of the enzyme activity that might otherwise occur in the absence of such substances in the sample. The amount of reduction of inhibition of enzyme activity is related to the amount of such substances other than sirolimus in the sample. The same assay is also carried out on sample portion 2, which is treated with FK506 ester to release sirolimus from endogenous binding substances in the sample. After conducting the assay, the amount of reduction of enzyme activity is measured and is related to the amount of both sirolimus and the substances other that sirolimus in the sample that bind to sirolimus antibody. Subtraction of the enzyme activity obtained from sample portion 1 from the enzyme activity obtained from sample portion 2 gives the amount of reduction of enzyme activity attributed to the amount of sirolimus in the sample.

Kits for Conducting Assays on the Sample Portions

The reagents for conducting a particular assay may be present in a kit useful for conveniently performing an assay for the determination of an analyte. In one embodiment a kit comprises in packaged combination reagents for sequestering an analyte, reagents for releasing an analyte from endogenous binding substances, an antibody for an analyte and other reagents for performing an assay, the nature of which depend upon the particular assay format. The reagents may each be in separate containers or various reagents can be combined in one or more containers depending on the cross-reactivity and stability of the reagents. The kit can further include other separately packaged reagents for conducting an assay such as additional sbp members, ancillary reagents such as an ancillary enzyme substrate, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method in accordance with the present embodiments as described above.

The following examples further describe the specific embodiments of the invention by way of illustration and not limitation and are intended to describe and not to limit the scope of the invention. Parts and percentages disclosed herein are by volume unless otherwise indicated.

EXAMPLES

All chemicals may be purchased from the Sigma-Aldrich Company (St. Louis Mo.) unless otherwise noted. Tacrolimus may be obtained from Astellas Pharma US. Inc., Deerfield Ill.

Testing is carried out using the DIMENSION® RxL analyzer, available from Siemens Healthcare Diagnostics Inc., Newark Del. The instrument is employed using ACMIA immunoassay technology. The ACMIA assay method is described in U.S. Pat. Nos. 7,186,518, 5,147,529, 5,128,103, 5,158,871, 4,661,408, 5,151,348, 5,302,532, 5,422,284, 5,447,870, and 5,434,051, the disclosures of which are incorporated herein in their entirety. In the embodiment of the ACMIA method used herein and discussed in more detail below, competition between tacrolimus analog on chrome particles and tacrolimus in patient samples for antibody for tacrolimus conjugated to an enzyme (the "conjugate") is utilized to determine the amount of tacrolimus in patient samples. Conjugate that binds to the tacrolimus analog on chrome particles is removed by magnetic separation. The enzymatic activity from conjugate remaining in the supernatant is measured and is directly proportional to the amount of tacrolimus in the patient sample. In the ACMIA assay format employed, the enzymatic activity observed when testing a sample containing no tacrolimus is indicative of the amount of enzymatic activity that is not bound to active antibody (i.e., cannot bind tacrolimus on chrome particles). The enzymatic activity observed when no chrome particle is present is indicative of the total amount of enzymatic activity in the conjugate. These values can be used to estimate the percent of enzymatic activity bound to active antibody.

Example 1

Automated Immunoassay for Tacrolimus

Two Assay Measurement Format to Eliminate False Results

In the method measurement result 1 is determined by means of an assay conducted on the sample where analyte in the sample is substantially sequestered and measurement result 2 is determined by means of the assay conducted on the sample where analyte in the sample is substantially non-sequestered. Measurement result 1 is subtracted from measurement result 2 to determine the concentration of analyte in the sample.

Preparation of Hemolytic Pretreatment Solution for Measurement Result 1. This pretreatment solution is prepared to contain 17.0 mg/mL PIPES™ 1.5 sodium salt (SesquiNa PIPES), 0.75 mg/mL EDTA Disodium, 2.5 mg/mL Saponin, 0.5% Proclin 300, 0.06 mg/mL Neomycin sulfate, pH 6.8. The solution also contains 1 µg/mL of a mouse monoclonal antibody (clone 1E2). This antibody has a strong binding for the FK506 parent drug but a weak binding for the FK506 analog (FK506-C22 oxime) that is used to coat the chromium dioxide solid phase. The function of this antibody is to scavenge the residual free drug in the absence of the drug displacer FKE. Table 1 shows the composition of the hemolysis reagent for use in hemolyzing a portion of a whole blood sample for assay for Tacrolimus (AI=as indicated).

TABLE 1

Hemolytic Pretreatment Reagent for Assay Measurement 1

| Name | Qty (per mL) | Function |
| --- | --- | --- |
| Anti-FK506 monoclonal Ab (1E2 clone) | 1 ug/mL | Makes residual FK506 molecules unaccessible to the assay Ab by binding |
| SesquiNa PIPES | 17 mg/mL | buffer |
| EDTA Disodium | 0.75 mg/mL | Preventing clot formation |
| Saponin | 2.5 mg/mL | blood cell lysis |
| Proclin 300 | 5.0 ml/L | preservative |
| Neomycin sulfate | 0.06 gm/L | preservative |

Preparation of Hemolytic Pretreatment Solution for Measurement Result 2. This pretreatment solution is prepared to contain 15 μg/mL of a FK-506 carbamate compound (or tacrolimus ester), 6.8 mg/mL PIPES™1.5 sodium salt, 0.3 mg/mL EDTA Disodium, 1.0 mg/mL Saponin, 0.2% Proclin 300, 0.024 mg/mL Neomycin sulfate and 0.99 mg/mL $NaN_3$, pH 6.5. The FKE concentration in the final reaction mixture is 1.2 μg/mL. Table 2 shows the composition of the hemolysis reagent for use in hemolyzing a portion of a whole blood sample for assay for Tacrolimus (AI=as indicated).

TABLE 2

| Name | Qty (per mL) | Function |
| --- | --- | --- |
| FK506 Ester | 5 ug/mL | dissociates tacrolimus from binding protein |
| SesquiNa PIPES | 17 mg/mL | buffer (pH 6.8) |
| EDTA Disodium | 0.75 mg/mL | Preventing clot formation |
| Saponin | 2.5 mg/mL | blood cell lysis |
| Proclin 300 | 5.0 ml/L | preservative |
| Neomycin sulfate | 0.06 gm/L | preservative |

Preparation of Anti-tacrolimus Antibody-β-galactosidase Conjugate. Monoclonal anti-tacrolimus antibody (clone 1H6 from Siemens Healthcare Diagnostics Inc, Glasgow, Del.) is conjugated to β-galactosidase using a standard heterobifunctional SMCC (succinimidyl trans-4-(N-maleimidylmethyl) cyclohexane-1-carboxylate) linker according to known techniques. The antibody conjugate solution contains approximately 7.5 μg/mL anti-tacrolimus antibody-β-galactosidase conjugate, 30 mg/mL protease free bovine serum albumin, 0.126 mg/mL $MgCl_2$, 0.03 mL/mL of ethylene glycol, 35.14 mg/mL PIPES 1.5 sodium salt, 50 mg/mL NaCl and beta-gal mutein (inactivated beta-galactosidase), pH 6.5.

Magnetic Chrome Particle Preparation. Tacrolimus chrome particles (immunoassay solid phase) are prepared by conjugating tacrolimus-C22 to fluorescein, which is used to pre-decorate anti-fluorescein antibody immobilized on chromium dioxide particles through glutaraldehyde. The chrome particle reagent contains approximately 2.5 mg/mL tacrolimus chrome particle slurry, 60.8 mg/mL trehalose dihydrate and 7.2 mg/mL CARBOWAX®.

Assay 1 for Measurement Result 1. 20 μL of a whole blood sample suspected of containing tacrolimus is mixed with the hemolytic pretreatment solution in a vessel on the DIMENSION® RxL analyzer. The whole blood is sampled from a standard cup by first mixing the blood with the ultrasonic sample probe. The mixing of whole blood sample with the pretreatment solution ensures the hemolysis of the whole blood. The displacement of the protein-bound tacrolimus molecules from their binding sites does not happen because the displacer, FKE, is not present in this assay. As a result, the signal generated from this assay contains <10% of the analyte signal (in most cases <5%) plus 100% of the assay matrix signal, which include signals generated from interference substances.

Anti-tacrolimus antibody-β-galactosidase conjugate (50 μL of above solution) is added next to each of the reaction vessels and the mixture is held for a period of time (10 to 15 minutes) and at a temperature of 43° C. to allow tacrolimus, if present, to react with the antibody reagent. Chrome particles with immobilized tacrolimus-CM0-DA10-Dexal are added (50 μL) to each of the reaction vessels and are allowed to bind unbound conjugate. The tacrolimus-bound anti-tacrolimus antibody-βgalactosidase conjugate does not bind to the chrome particles but remains in the supernatant when a magnetic field is applied to the above reaction mixtures to separate the solution from the chrome particles. The tacrolimus-bound conjugate is detected by transferring the supernatant from each of the reaction vessels to a photometric cuvette and measuring the enzymatic rate of the conjugate in the presence of chlorophenol red-β-D-galactopyranoside (CPRG). The rate for each reaction vessel is measured bichromatically at 577 and 700 nm.

Assay 2 for Measurement Result 2. The principle and operation of the ACMIA assay for tacrolimus for detection of false results is as follows: 20 μL of a whole blood sample suspected of containing tacrolimus is mixed with the hemolytic pretreatment solution in a vessel on the DIMENSION® RxL analyzer. The whole blood is sampled from a standard cup by first mixing the blood with the ultrasonic sample probe. The mixing of whole blood sample with the pretreatment solution ensures the hemolysis of the whole blood and the displacement of the protein-bound tacrolimus molecules from their binding sites when the tacrolimus carbamate (FKE) molecules were present. As a result, the signal generated from this assay contains <100% of the analyte signal plus 100% of the assay matrix signal, which include signals generated from potential interference substances.

Anti-tacrolimus antibody-β-galactosidase conjugate (50 μL) is added next to each of the reaction vessels and the mixture is held for a period of time (10 to 15 minutes) and at a temperature of 43° C. to allow tacrolimus, if present, to react with the antibody reagent. Chrome particles with immobilized tacrolimus-CMO-DA10-Dexal are added (50 μL) to each of the reaction vessels and are allowed to bind unbound conjugate. The tacrolimus-bound anti-tacrolimus antibody-β-galactosidase conjugate does not bind to the chrome particles but remains in the supernatant when a magnetic field is applied to the above reaction mixtures to separate the solution from the chrome particles. The tacrolimus-bound conjugate is detected by transferring the supernatant from each of the reaction vessels to a photometric cuvette and measuring the enzymatic rate of the conjugate in the presence of chlorophenol red-β-D-galactopyranoside (CPRG). The rate for each reaction vessel is measured bichromatically at 577 and 700 nm.

Measurement result 1 is determined by the above mentioned assay 1 conducted on the sample where tacrolimus in the sample is substantially sequestered. Measurement result 2 is determined by the above mentioned assay 2 conducted on the sample where tacrolimus in the sample is substantially non-sequestered. Measurement result 1 is subtracted from measurement result 2 to determine the concentration of analyte in the sample.

Two transplant recipient patient samples that demonstrated falsely elevated tacrolimus values by the conventional no-manual pretreatment ACMIA method were tested using the two assay method described above. These two patient samples contained little tacrolimus drug as tested by a manual pretreatment method (e.g., EMIT). Table 3 shows the result comparison between the conventional ACMIA method and the two measurement ACMIA method. As can be seen, false positive results were mitigated by the two measurement assay approach in accordance with present embodiments.

TABLE 3

| False Positive Sample | Conventional ACMIA Method Tacrolimus (ng/mL) | Two Measurement ACMIA Method Tacrolimus (ng/mL) |
| --- | --- | --- |
| 1 | 18.0 | −0.3 |
| 2 | 12.7 | 1.2 |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for reducing false results in an assay measurement for determining a concentration of an analyte in a sample suspected of containing the analyte, the method comprising:
   (a) determining a measurement result 1 by means of an assay conducted on a portion of the sample where analyte in the sample is substantially sequestered by addition of a sequestering agent that does not interfere with reagents employed in the assay, wherein the amount of sequestering agent that is added to the sample is that which is sufficient to sequester the analyte so that signal obtained in an assay on the sample is representative solely of components in the sample and not of analyte,
   (b) determining a measurement result 2 by means of the assay conducted on another portion of the sample where analyte in the sample is substantially non-sequestered by addition of a releasing agent,
   wherein the assay comprises:
   (i) adding reagents for determining the concentration of the analyte in the sample to a medium comprising the sample of step (a) and to a medium comprising the sample of step (b) wherein the reagents comprise at least one antibody for the analyte, and
   (ii) measuring in step (a) an amount of a complex comprising the antibody for the analyte to determine measurement result 1 and measuring in step (b) an amount of a complex comprising the antibody for the analyte to determine measurement result 2,
   (c) subtracting measurement result 1 from measurement result 2 to determine the concentration of analyte in the sample.

2. The method of claim 1 wherein the sample is a body excretion, body aspirant, body excisant or body extractant.

3. The method according to claim 1 wherein the assay method is a homogeneous assay method.

4. The method according to claim 1 wherein the reagents in step (i) further comprise an analog of the analyte that comprises a label and that competes with the analyte for binding to the antibody for the analyte.

5. The method according to claim 1 wherein in step (i) a second antibody is added to the medium wherein the second antibody binds to a complex comprising the antibody for the analyte.

6. The method according to claim 5 wherein at least one of the antibody for the analyte or the second antibody comprises a label.

7. The method according to claim 1 wherein the reagents further comprise a labeled reagent.

8. The method according to claim 1 wherein the reagents further comprise a particulate reagent.

9. The method according to claim 1 wherein the reagents further comprise an enzyme-labeled reagent and a magnetic particulate reagent.

10. The method according to claim 1 wherein the releasing agent is added to the medium prior to or during step (b).

* * * * *